United States Patent
Goto

(10) Patent No.: US 9,839,351 B2
(45) Date of Patent: Dec. 12, 2017

(54) IMAGE GENERATING APPARATUS, IMAGE GENERATING METHOD, AND PROGRAM

(71) Applicant: CANON KABUSHIKI KAISHA, Tokyo (JP)

(72) Inventor: Atsushi Goto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 3 days.

(21) Appl. No.: 15/140,221

(22) Filed: Apr. 27, 2016

(65) Prior Publication Data

US 2016/0317027 A1 Nov. 3, 2016

(30) Foreign Application Priority Data

May 1, 2015 (JP) ................. 2015-094343

(51) Int. Cl.
 *A61B 3/14* (2006.01)
 *A61B 3/00* (2006.01)
 *A61B 3/10* (2006.01)
 *A61B 3/12* (2006.01)

(52) U.S. Cl.
 CPC ............ *A61B 3/102* (2013.01); *A61B 3/0025* (2013.01); *A61B 3/0058* (2013.01); *A61B 3/1233* (2013.01)

(58) Field of Classification Search
 CPC ..... A61B 3/102; A61B 3/1233; A61B 3/0025; A61B 3/0058
 USPC .................................................. 351/206, 246
 See application file for complete search history.

(56) References Cited

U.S. PATENT DOCUMENTS 8,433,393 B2  4/2013  Sharma et al.
2014/0221827 A1  8/2014  Motaghiannezam et al.

OTHER PUBLICATIONS

Makita, S., et al., "Optical coherence angiography", Optics Express, Aug. 21, 2006, pp. 7821-7840, vol. 14, No. 17.
Fingler, J., et al., "Mobility and transverse flow visualization using phase variance contrast with spectral domain optical coherence tomography", Optics Express, Oct. 1, 2007, pp. 12636-12653, vol. 15, No. 20.
Mariampillai, A., et al., "Speckle variance detection of microvasculature using swept-source optical coherence tomography", Optics Letters, Jul. 1, 2008, pp. 1530-1532, vol. 33, No. 13.
Mariampillai, A., et al., "Optimized speckle variance OCT imaging of microvasculature", Optics Letters, Apr. 15, 2010, pp. 1257-1259, vol. 35, No. 8.

*Primary Examiner* — Jack Dinh
(74) *Attorney, Agent, or Firm* — Canon USA Inc., IP Division

(57) ABSTRACT

A method of generating a tomographic image using optical coherence tomography includes: a data obtaining step of obtaining a plurality of pieces of tomographic image data each indicating a tomogram at substantially the same position of an object; a removing step of removing an outlier from the plurality of pieces of tomographic image data; a computation step of computing a motion contrast value based on the plurality of pieces of tomographic image data from which the outlier is removed; and a generation step of generating a motion contrast image of the object based on the motion contrast value.

20 Claims, 10 Drawing Sheets

IMAGE GENERATING APPARATUS, IMAGE GENERATING METHOD, AND PROGRAM

BACKGROUND

Field

This patent application relates to an image generating apparatus, an image generating method, and a program.

Description of the Related Art

As a method for obtaining a tomographic image of an object such as an organism in a nondestructive and noninvasive manner, optical coherence tomography (hereinafter, referred to as "OCT") has been put into use. In the OCT, in particular, a tomographic image is widely used in ophthalmic diagnosis.

In OCT, by making light reflected on a measurement object and light reflected on a reference mirror interfere with each other and analyzing the interfering light, a tomographic image of the object is obtained. As an image acquiring apparatus by optical coherence tomography, time-domain OCT in which depth information of a measurement object is obtained by changing a position of a reference mirror, Spectral Domain Optical Coherence Tomography (SD-OCT) in which interfering light is converted into a spectrum by using a broadband light source and an interfering signal is obtained, and Swept Source Optical Coherence Tomography (SS-OCT) in which an interfering signal is obtained by using a variable wavelength light source are known. Note that, SD-OCT and SS-OCT are also called FD-OCT (Fourier Domain-Optical Coherence Tomography) collectively.

In recent years, an angiography method using the FD-OCT has been proposed and is called OCT angiography.

Fluorescence imaging, which is a conventional angiography method, is invasive and requires injection of a fluorescent dye (for example, fluorescein and indocyanine green) into a body. Further, in conventional fluorescence imaging, a blood vessel serving as a passageway for the fluorescent dye is two-dimensionally displayed.

On the other hand, the OCT angiography is noninvasive because the usage of interfering light obviates the need of fluorescent dye. In addition, a signal of the OCT imaging allows three-dimensional display of a vascular network. Further, the OCT angiography is attracting attention because it has higher resolution compared to fluorescence imaging using a fundus camera and a scanning laser ophthalmoscope (SLO), and allows visualization of a microvessel of the fundus of an eye.

Various methods are proposed for the OCT angiography according to a difference of an angiography method. A method using Doppler shift by blood flow, which is disclosed in "Optical Coherence Angiography" by Makita et al., (Optics Express, 14 (17), 7821-7840 (2006), and a method using phase variance of an OCT signal by blood flow, which is disclosed in "Mobility and transverse flow visualization using phase variance contrast with spectral domain optical coherence tomography" by Fingler et al., (Optics Express. Vol. 15, No. 20. pp 12637-12653 (2007)) are proposed. Further, "Speckle variance detection of microvasculature using swept-source optical coherence tomography" (Optics Letters Vol. 33, Iss. 13, pp. 1530-1532 (2008)), "Optimized speckle variance OCT imaging of microvasculature" by Mariampillai et al., (Optics Letters 35, 1257-1259 (2010)), and the specification of U.S. Patent Application Publication No. 2014/221827 disclose a method using intensity variance of an OCT signal by blood flow. In addition, the specification of U.S. Pat. No. 8,433,393 proposes, for example, a method using changes of a phase and an intensity of an OCT signal by blood flow.

However, in the aforementioned methods for detecting blood flow, other than the OCT angiography using Doppler shift, noise derived from a motion of an object (bulk motion noise) is generated. This is because in OCT angiography interfering signals are obtained by measuring almost the same portion for a plurality of times, to generate an image, and therefore a measurement value changes regardless of the blood flow when the object moves during image capturing and the change is erroneously detected as the change of the blood flow. For example, in a case of fast movement by involuntary movement of an eyeball, the bulk motion noise appears in an OCT angiography image as partially linear noise in a main scanning direction.

U.S. Patent Application Publication No. 2014/221827 discloses, as a first method for reducing bulk motion noise, a method for dividing a wavelength spectrum of an interfering signal into a plurality of pieces and then performing frequency analysis to thereby reduce the bulk motion noise instead of reducing resolution in a depth direction. Further, as a second method, a method for positioning tomographic images obtained by performing image capturing a plurality of times to thereby reduce the bulk motion noise is disclosed. Disclosed as a third method is a method for computing decorrelation of the tomographic images obtained by performing image capturing a plurality of times in a region at a fixed depth from a retinal surface layer, comparing median values of decorrelation values of decorrelation images for each frame, and removing a frame of an abnormal decorrelation image.

However, the first method of U.S. Patent Application Publication No. 2014/221827 has no effect on the bulk motion noise due to movement of the fundus in a plane direction (directions in a plane perpendicular to a direction of an eye axial length).

Further, with the second method, it is possible to roughly position the tomographic images, but a positional deviation due to distortion of the tomographic images, which is generated during measurement of the tomographic images because of movement of the object for a short period of time is not solved, so that the bulk motion is not reduced in some cases.

In the third method, detection ability is inferior because a part of areas of the tomographic images is used for noise detection. Further, even when the detection is performed successfully, even normal data of the tomographic images having no noise is removed.

SUMMARY

A method of generating a tomographic image using optical coherence tomography, including: a data obtaining step of obtaining a plurality of pieces of tomographic image data each indicating a tomogram at substantially the same portion of an object; a removing step of removing an outlier from the plurality of pieces of tomographic image data; a computation step of computing a motion contrast value based on the plurality of pieces of tomographic image data from which the outlier is removed; and a generation step of generating a motion contrast image of the object based on the motion contrast value.

Further features of the present invention will become apparent from the following description of exemplary embodiments with reference to the attached drawings.

DESCRIPTION OF THE EMBODIMENTS

Hereinafter, an image capturing apparatus according to the present embodiment will be described with reference to the accompanying drawings. Note that, the configuration indicated in the following embodiments is only exemplary, and the invention is not limited to the following embodiments.

First Embodiment

[Overall Configuration of Image Capturing Apparatus]

Figure 1:
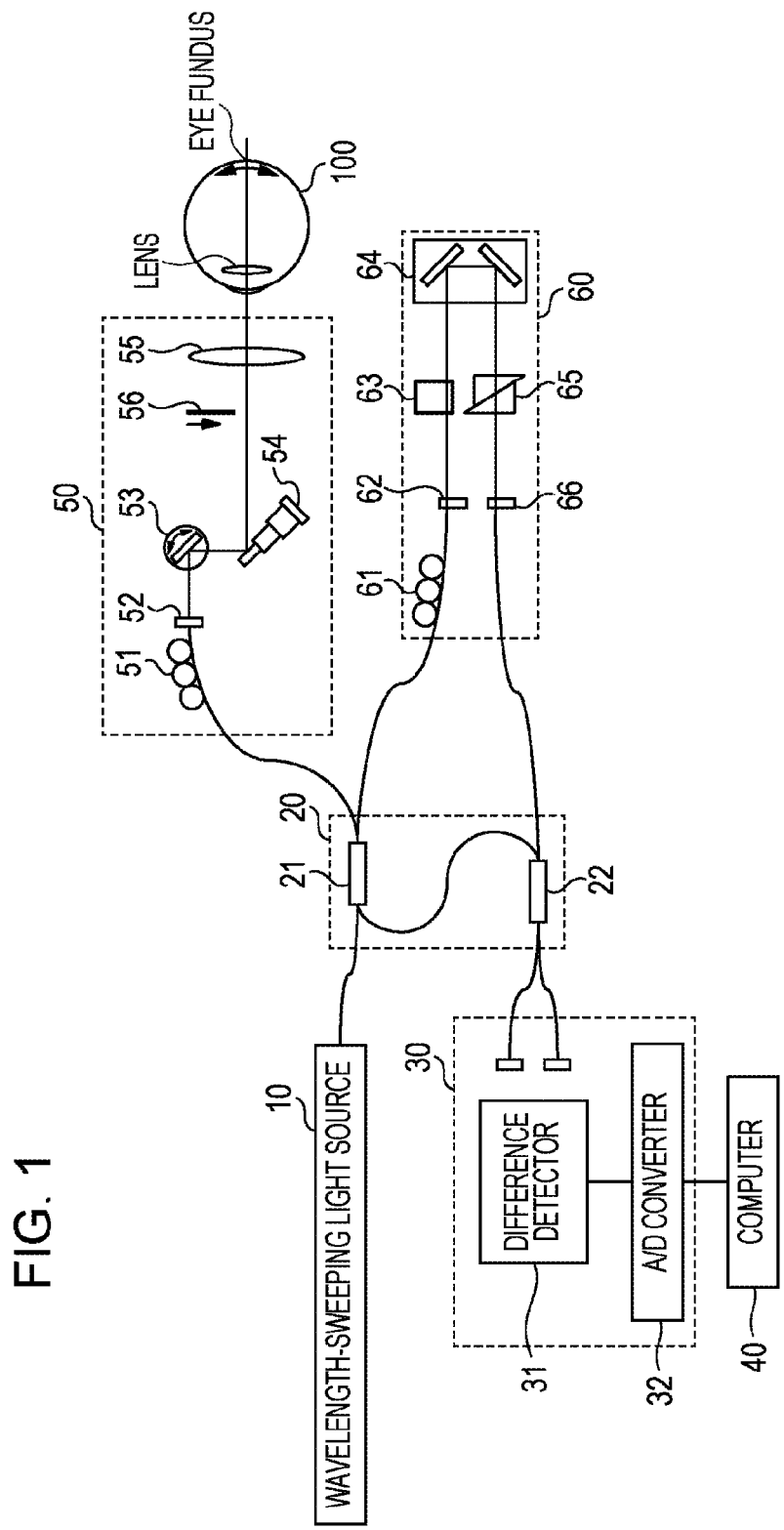
FIG. 1 is a schematic view illustrating one example of an overall configuration of an image capturing apparatus according to one embodiment.

FIG. 1 illustrates a configuration example of an image capturing apparatus (OCT apparatus) using optical coherence tomography in the present exemplary embodiment. Illustrated is a configuration in a case of SS-OCT, but a similar effect may be realized also by an OCT apparatus of other system.

The present OCT apparatus has a wavelength-sweeping light source 10, an optical signal branching/combining unit 20, a measurement arm 50, a reference arm 60, a detection unit 30 for detecting interfering light, and a computer 40 for obtaining retina information of a human eye 100 based on the interfering light.

The wavelength-sweeping light source 10 emits light, for example, with a wavelength of 980 nm to 1100 nm at a frequency of 100 kHz (A-scan rate). The wavelength and the frequency are exemplifications and the invention is not limited to the values described above. Similarly in the following embodiments, described numerical values are exemplifications and the invention is not intended to be limited to the described numerical values.

Note that, an object in the present exemplary embodiment is set as a human eye (eye fundus), but, without limitation thereto, the object may be, for example, a skin or the like. Moreover, an object to be imaged in the present exemplary embodiment is set as the eye fundus, but the object to be imaged may be an anterior eye part.

The OCT interfering unit 20 has couplers 21 and 22. First, the coupler 21 branches light emitted from the wavelength-sweeping light source 10 into irradiation light to be irradiated to the eye fundus and reference light.

The irradiation light is irradiated to the human eye 100 via the measurement arm 50. More specifically, the irradiation light incident on the measurement arm 50 has a polarization state adjusted by a polarizing controller 51, and is then emitted from a collimator 52 as spatial light. After that, the irradiation light is irradiated to the eye fundus of the human eye 100 through an X-axis scanner 53, a Y-axis scanner 54, a shutter 56, and a focus lens 55. Note that, the X-axis scanner 53 and the Y-axis scanner 54 are scanning units having a function of scanning the eye fundus with irradiation light. An irradiation position of the irradiation light to the eye fundus is changed by the scanning units.

Reflected light from the eye fundus passes through the coupler 21 via the same path such as the focus lens 55 again and is incident on the coupler 22. Note that, by performing measurement with the shutter 56 closed, it is possible to perform background measurement by cutting off the reflected light from the human eye 100.

On the other hand, the reference light is incident on the coupler 22 via the reference arm 60. More specifically, the reference light incident on the reference arm 60 has a polarization state adjusted by a polarizing controller 61, and is then emitted from a collimator 62 as spatial light. After that, the reference light passes through a dispersion-compensating glass 63, an optical system for adjustment of optical path length 64, and a dispersion-adjustment prism pair 65, is incident on an optical fiber through a collimator lens 66, emitted from the reference arm 60, and is incident on the coupler 22.

The reflected light from the human eye 100, which has passed through the measurement arm 50, and the reference light which has passed through the reference arm 60 are combined and interfered by the coupler 22. Then, the interfering light is detected by the detection unit 30. The detection unit 30 has a difference detector 31, and an A/D converter 32. First, in the detector 30, the interfering light branched by the coupler 22 is detected by the difference detector 31. An OCT interfering signal converted into an electrical signal by the difference detector 31 is then converted into a digital signal by the A/D converter 32. In this case, sampling of the interfering light by the difference detector 31 is performed at regular wave-number intervals based on a k-clock signal transmitted by a clock generation unit incorporated in the wavelength-sweeping light source 10. The digital signal output by the A/D converter 32 is sent to the computer 40. Then, the computer 40 performs signal processing for the interfering signal converted into the digital signal and computes an OCT angiography image.

Specific contents of the signal processing performed by the computer 40 will be described below.

Here, obtaining of information of one point of the human eye 100 in a depth direction is called A-scan. Further, obtaining of a two-dimensional tomographic image in a direction orthogonal to the A-scan is called B-scan, and obtaining of a two-dimensional tomographic image along a direction vertical to the two-dimensional tomographic image of the B-scan is called C-scan.

Note that, each of the X-axis scanner 53 and the Y-axis scanner 54 is formed of a mirror, and rotation axes of each of mirrors are arranged so as to be orthogonal to each other. The X-axis scanner 53 performs scanning in an X-axis direction and the Y-axis scanner 54 performs scanning in a Y-axis direction. The X-axis direction and the Y-axis direction are directions vertical to an eye axis direction of an eyeball, and are vertical to each other. Line scanning directions of the B-scan and the C-scan may not match the X-axis direction or the Y-axis direction. Thus, the line scanning directions of the B-scan and the C-scan are able to be decided as appropriate according to a two-dimensional tomographic image or a three-dimensional tomographic image desired to be captured.

Figure 2:
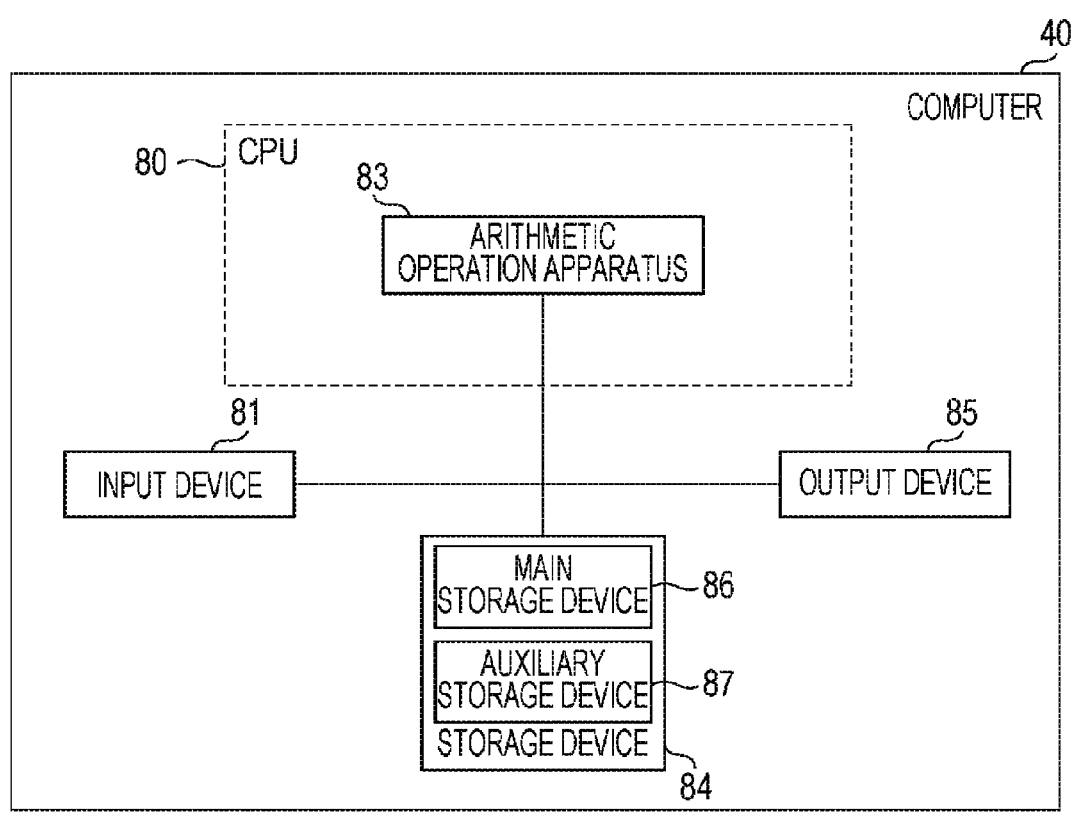
FIG. 2 illustrates one example of a hardware configuration of a computer.

Next, description will be given for a hardware configuration of the computer 40 with reference to FIG. 2 and for a functional configuration thereof with reference to FIG. 3. The computer 40 includes, as illustrated in FIG. 2, a central processing unit (CPU) 80, a storage device 84, an input device 81 (such as a mouse and a keyboard), and an output device 85 (such as a display). The CPU 80 includes an arithmetic operation apparatus 83. The storage device 84 is formed of a main storage device 86 (such as a ROM or a RAM), and an auxiliary storage device 87 (such as a magnetic disc device and SSD (Solid State Drive)).

Further, various functions executed by the CPU 80 will be described with reference to FIG. 3.

Figure 3:
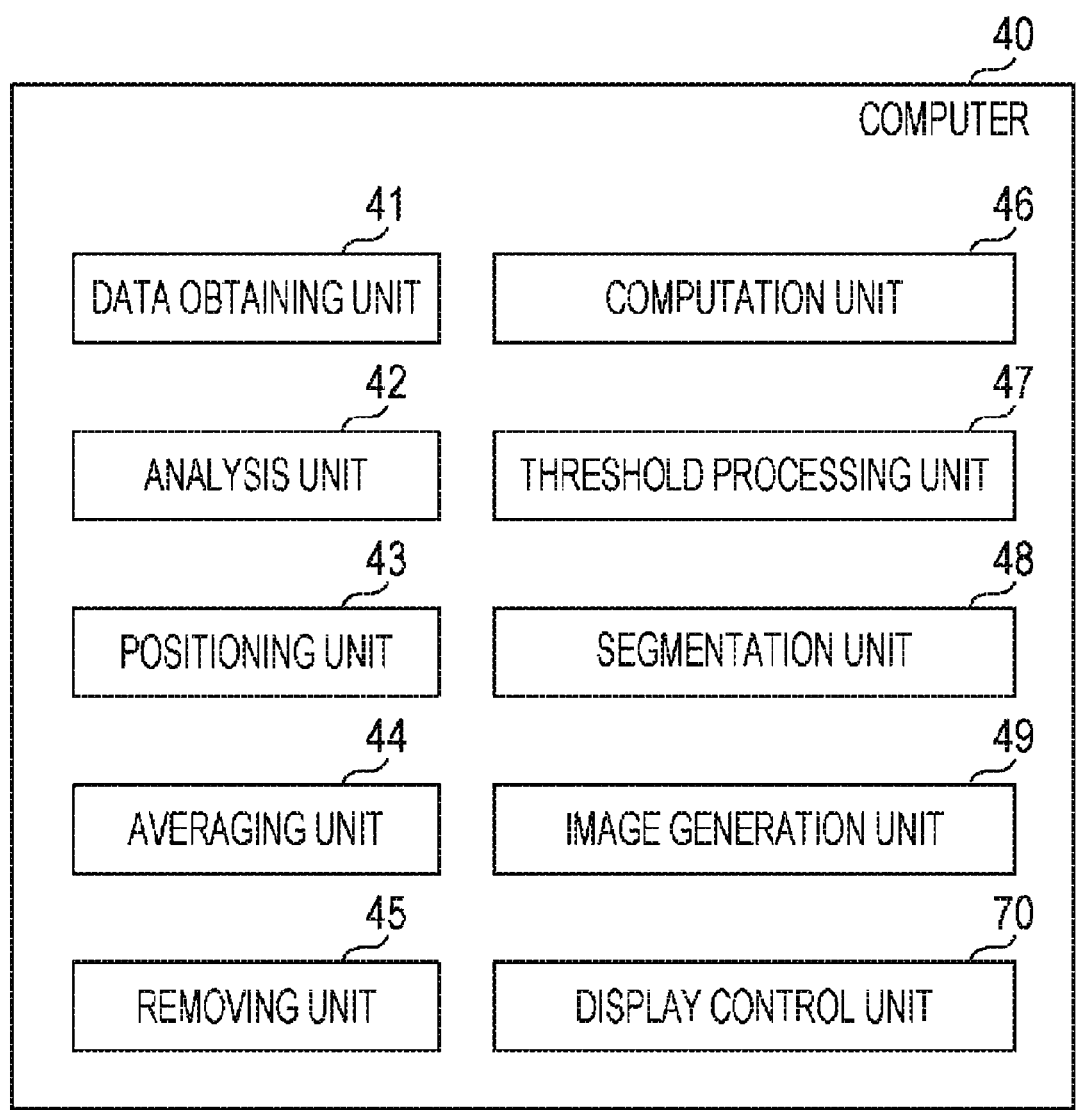
FIG. 3 illustrates one example of a functional configuration of the computer.

The arithmetic operation apparatus 83 included in the CPU 80 functions as a data obtaining unit 41, an analysis unit 42, a positioning unit 43, an averaging unit 44, a removing unit 45, a computation unit 46, a threshold processing unit 47, a segmentation unit 48, an image generation unit 49, and a display control unit 70 in FIG. 3 by executing a program stored in the storage device 84. Further, the arithmetic operation apparatus 83 controls order of executing the aforementioned units.

Note that, the computer 40 may include one or more CPUs 80 and storage devices 84. That is, when at least one or more processing units (CPUs) are connected to at least one or more storage devices and at least one or more processing units execute a program stored in at least one or more storage devices, the computer 40 functions as each of the aforementioned units. Note that, the processing unit is not limited to the CPU and may be an FPGA or the like.

By controlling the OCT apparatus, the data obtaining unit 41 obtains an interfering signal in accordance with procedure for obtaining an interfering signal, which will be described below, and stores the interfering signal in the main storage device 86. Note that, the data obtaining unit 41 may be a unit configured to read an interfering signal saved in the auxiliary storage device 87 in advance.

Specifically, the data obtaining unit 41 obtains an output of the A/D converter 32. That is, the data obtaining unit 41 obtains a digital signal of interfering light (interfering signal) of returned light of measurement light, which is obtained by scanning an eye to be inspected, from the eye to be inspected, and reference light. Note that, the obtaining unit 41 also functions as a unit configured to control the X-axis scanner 53 and the Y-axis scanner 54.

The analysis unit 42 performs frequency analysis of the digital signal of the interfering light (interfering signal). Specifically, the analysis unit 42 generates an OCT complex signal composed of a phase and amplitude by applying Fast Fourier Transform (FFT) to the interfering signal. Note that, a maximum entropy method may be used for the frequency analysis.

Further, the analysis unit 42 obtains a tomographic image indicating an intensity (hereinafter, also simply referred to as a tomographic image) by squaring an absolute value of the OCT complex signal having been subjected to the frequency analysis and compute the intensity. This tomographic image corresponds to one example of tomographic image data indicating a tomogram of the eye fundus of the eye to be inspected. In other words, the tomographic image data is data obtained by performing frequency analysis for an output of the detection unit (sensor) which has received the interfering light. That is, when substantially the same position of the eye fundus of the eye to be inspected is scanned with measurement light for a plurality of times, the analysis unit 42 obtains a plurality of pieces of tomographic image data each indicating substantially the same position of an object. That is, the processing performed by the data obtaining unit 41 and the analysis unit 42 corresponds to one example of a data obtaining step of obtaining a plurality of pieces of tomographic image data each indicating a tomogram at substantially the same position of an object.

Note that, the plurality of pieces of tomographic image data are data obtained by performing scanning with the measurement light at different timings. Further, the analysis unit 42 extracts the phase from the OCT complex signal.

The positioning unit 43 performs positioning of a plurality of tomographic images. In the present embodiment, the positioning unit 42 performs positioning of the plurality of tomographic images obtained by scanning substantially the same position of the eye fundus of the eye to be inspected with the measurement light for a plurality of times. More specifically, the positioning unit 43 performs positioning of the plurality of pieces of tomographic image data before the computation unit 46 computes a motion contrast value. The processing by the positioning unit 43 corresponds to one example of a positioning step of positioning the plurality of pieces of tomographic image data.

The positioning of the tomographic images can be realized by various known methods. The positioning unit 43 performs positioning of the plurality of tomographic images, for example, so as to achieve the maximum level of correlation between the tomographic images. Note that, the positioning may not be required when the object is not a sample which moves like the eye. Further, even if the object is the eye, positioning is not required when tracking performance is high. That is, the positioning of the tomographic images by the positioning unit 43 is inessential.

The averaging unit 44 computes an average value of the plurality of tomographic images positioned by the positioning unit 43 to thereby generate an averaged image. The averaged image is a tomographic image in which signal intensities of the tomographic images are averaged. This averaged image is called an intensity averaged image in some cases.

The removing unit 45 removes an outlier from the plurality of tomographic images obtained by scanning substantially the same position of the eye fundus of the eye to be inspected with the measurement light for the plurality of times. For example, the removing unit 45 removes, as the outlier, the signal intensity whose deviation amount from the average value of the signal intensities at the corresponding positions of the plurality of tomographic images is greater than a predetermined value. That is, the processing performed by the removing unit 45 corresponds to one example of a removing step of removing an outlier from the plurality of pieces of tomographic image data. The removing step is performed after the positioning step is performed.

Note that, a specific removing method will be indicated in procedure for signal processing described below.

The computation unit 46 computes a motion contrast feature quantity (hereinafter, also referred to as a motion contrast value) from the tomographic image data from which the outlier is removed by the removing unit 45. The processing performed by the computation unit 46 corresponds to one example of a computation step of computing a motion contrast value based on the plurality of pieces of tomographic image data from which the outlier is removed.

Here, the motion contrast is a contrast between a flowing tissue (for example, blood) and a tissue without a flow of tissues of the object, and a feature quantity representing the motion contrast is defined as the motion contrast feature quantity. Here it should be noted that in medical terms blood is living tissue made up of liquid and solids. The liquid part of blood is called plasma and includes water and proteins; the solid part of blood contains red and white cells and platelets. The motion contrast reveals the difference between a part of a body having flowing tissue and another part without flowing tissue.

The motion contrast feature quantity is computed based on a change in the data of the plurality of tomographic images obtained by scanning substantially the same position with the measurement light for the plurality of times. For example, the computation unit 46 computes, as the motion contrast feature quantity, dispersion of the signal intensities (luminance) of the plurality of tomographic images which are positioned. More specifically, the computation unit 46 computes, as the motion contrast feature quantity, dispersion of the signal intensities at the corresponding positions of the plurality of tomographic images which are positioned. For example, since the signal intensity of an image corresponding to the blood vessel at a predetermined time and the signal intensity of an image corresponding to the blood vessel at a time different from the predetermined time are different from each other according to blood flow, a dispersion value of a portion corresponding to the blood vessel is greater than a dispersion value of a portion having no flow such as blood flow. That is, the motion contrast value is a value which increases as the change in the object among the plurality of pieces of tomographic image data is great. Accordingly, the motion contrast can be represented by generating an image based on the dispersion value. Note that, the motion contrast feature quantity is not limited to the dispersion value, and may be any of a standard deviation, a difference value, a decorrelation value, and a correlation value. Further, a phase may be used instead of the signal intensity. That is, the computation unit 46 computes, as the motion contrast feature quantity, a variation of the signal intensities or phases between the plurality of pieces of tomographic image data.

The threshold processing unit 47 sets a threshold to tomographic images indicating the intensities, and sets a value of the motion contrast feature quantity of a region having the signal intensity below the threshold to 0.

For example, the threshold processing unit 47 compares the signal intensity of the averaged image to the threshold. When the signal intensity at a predetermined position of the averaged image is smaller than the threshold, the threshold processing unit 47 causes the motion contrast feature quantity obtained based on the dispersion and the like at the predetermined position of the averaged image to have a value different from the feature quantity indicating the blood vessel. For example, when the signal intensity of the averaged image is smaller than the threshold, the threshold processing unit 47 sets the motion contrast feature quantity obtained based on the dispersion and the like to 0. That is, the threshold processing unit 47 sets the motion contrast value when a representative value indicating the signal intensity is smaller than the threshold to be a value smaller than the motion contrast value when the representative value indicating the signal intensity is greater than the threshold. Note that, the threshold processing unit 47 may compare the signal intensity of the averaged image to the threshold before the computation unit 46 computes, as the motion contrast feature quantity, the dispersion of the signal intensities of the plurality of tomographic images. For example, when the signal intensity of the averaged image is smaller than the threshold, the threshold processing unit 47 computes the motion contrast feature quantity as 0. Further, when the signal intensity of the averaged image is greater than the threshold, the computation unit 46 computes, as the motion contrast feature quantity, the dispersion of the signal intensities of the plurality of tomographic images.

Figure 9:
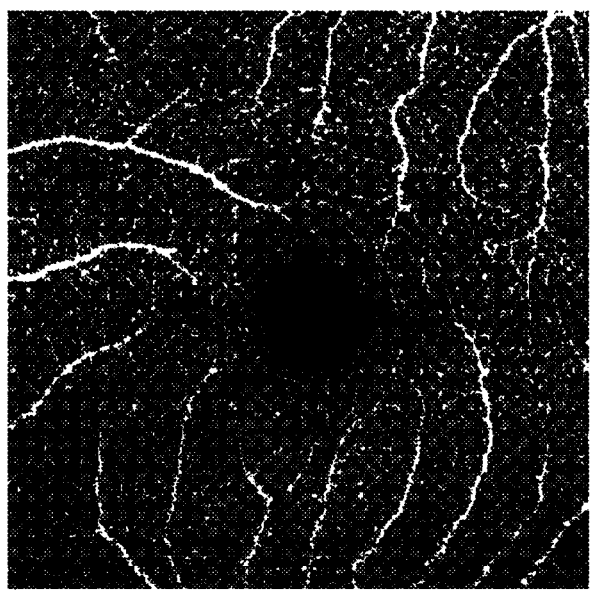
FIG. 9 illustrates one example of an OCT angiography image in the present embodiment.

Here, a black portion of an image illustrated in FIG. 9 or the like indicates that the feature quantity is 0. Note that, the motion contrast feature quantity may not be set to be completely 0, but a value near 0. On the other hand, when the signal intensity of the averaged image is greater than the threshold, the threshold processing unit 47 maintains the motion contrast feature quantity obtained based on the dispersion and the like.

The segmentation unit 48 detects a layer of the retina from the tomographic image generated by the averaging unit 44 and extracts layer boundaries between regions of the layer of the retina. Specific method for the detection will be indicated in procedure for signal processing described below.

Figure 8:
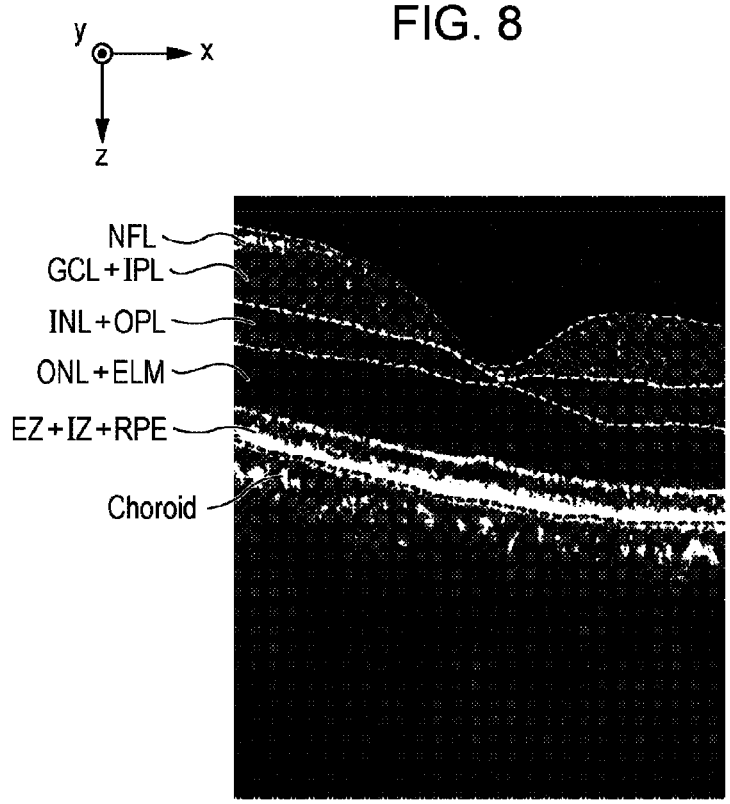
FIG. 8 is a diagram for explaining one example of a result of segmentation.

When the computation unit 46 computes a three-dimensional motion contrast feature quantity (three-dimensional data) from three-dimensional tomographic image data, the image generation unit 49 is able to generate a three-dimensional OCT angiography image. The image generation unit 49 is also able to generate a two-dimensional OCT angiography image obtained by projection or integration in a depth range of any retina direction of the three-dimensional OCT angiography image. That is, the image generation unit 49 generates the motion contrast image in a two-dimensional manner by performing projection or integration, in the depth direction, for the motion contrast value in a predetermined range of a depth direction of the object. FIG. 8 illustrates one example of a two-dimensional OCT angiography image (also referred to as an en-face blood vessel image, or simply as an en-face image).

More specifically, the three-dimensional motion contrast feature quantity computed by the computation unit 46 is segmented by using the segmentation data extracted by the segmentation unit 48. Further, the image generation unit 49 extracts any layer of the retina, and projects or integrates the motion contrast value for a two-dimensional direction (X-direction and Y-direction) to thereby generate an OCT image (en-face image) which two-dimensionally represents the layer of the retina of the eye fundus.

Note that, since the motion contrast feature quantity and a result of the segmentation are obtained from the same tomographic image, the motion contrast feature quantity and the result of the segmentation are associated with each other. Thus, with the association of the motion contrast feature quantity and the result of the segmentation, the image generation unit 49 is able to cut off the motion contrast feature quantity of any layer from three-dimensional volume data of the motion contrast feature quantity.

The image generation unit 49 is further able to cut off a depth range of any retina direction from the three-dimensional OCT angiography image and generate a partial three-dimensional OCT angiography image. That is, the image generation unit 49 generates the three-dimensional motion contrast image based on the motion contrast value in a predetermined range in the depth direction of the object.

Note that, the depth range of the retina can be set by an inspection operator (operator). For example, candidates of selectable layer, such as a layer from IS/OS to RPE, and a layer from RPE to BM, are displayed on a display unit 70. The inspection operator selects a predetermined layer from the displayed candidates of the layers. The image generation unit 49 may generate the two-dimensional OCT angiography image (en-face blood vessel image) or the partial three-dimensional OCT angiography image by integrating the retina in the depth direction of the layer selected by the inspection operator.

The image generation unit 49 may generate an OCT angiography image corresponding to the tomographic image by using the motion contrast feature quantity.

As described above, the processing by the image generation unit 49 corresponds to one example of a generation step of generating a motion contrast image of the object based on the motion contrast value.

The display control unit 70 causes the display device 85 serving as a display unit to display various information. More specifically, the display control unit 70 causes the display device 85 serving as the display to display the OCT angiography image generated by the image generation unit 49. That is, the processing by the display control unit 70 corresponds to one example of a display control step of causing a display unit to display the motion contrast image generated at the generation step.

[Scanning Pattern]

Next, one example of a scanning pattern of the present embodiment will be described with reference to FIG. 4.

In the OCT angiography, for measuring a time change of the OCT angiography signal due to blood flow, a plurality of interfering signal data sets obtained by repeatedly measuring almost the same portion for at least two or more times are required. In FIG. 4, a direction of irradiation light incident to an object is in the z-axis (irradiation in the z-axis or depth direction), and directions of a plane orthogonal to the z-axis (depth direction), that is, directions of the plane of the eye fundus are an x-axis and a y-axis.

Figure 4:
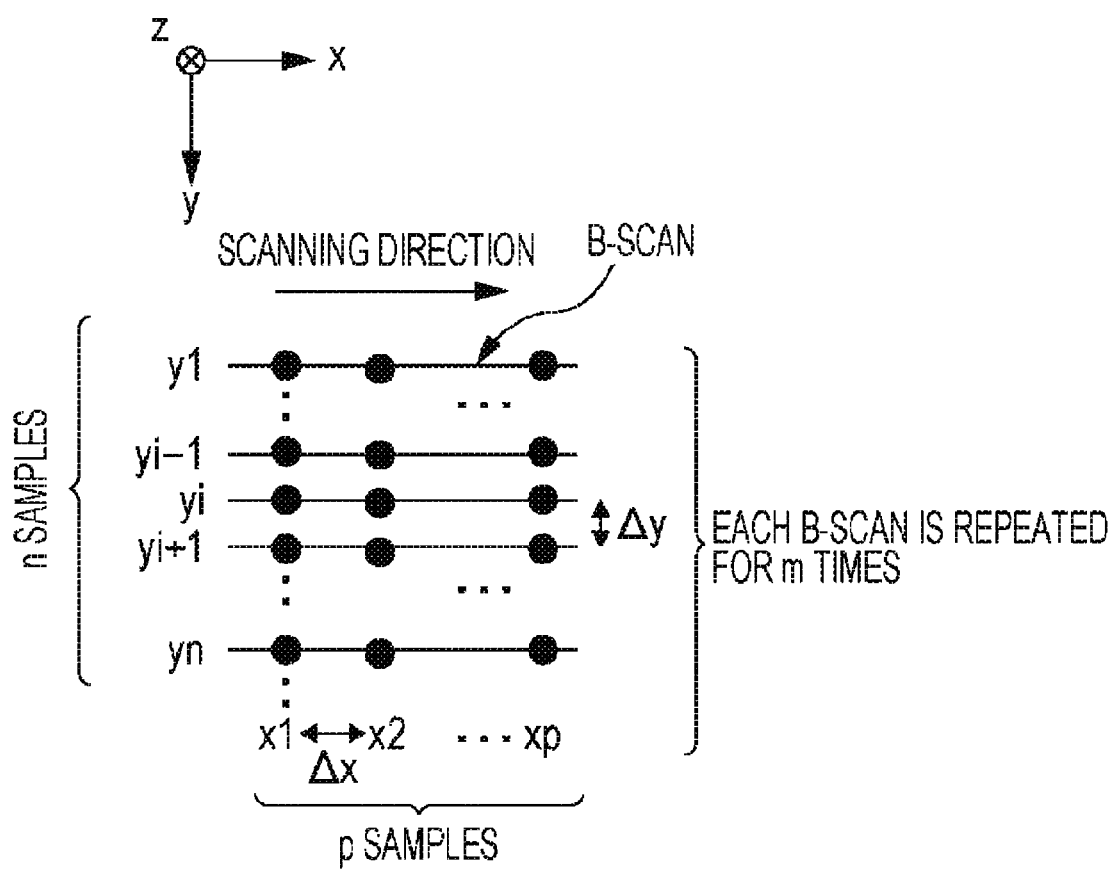
FIG. 4 illustrates one example of a scanning pattern in the present embodiment.

In FIG. 4, y1 to yn denote B-scans at different y-positions and n denotes the number of samples in a y-scanning direction. x1 to xp denote sample positions in an x-scanning direction and p denotes the number of samples in the x-scanning direction, which form the B-scan. Δx denotes an interval between adjacent x-positions (x-pitch) and Δy denotes an interval between adjacent y-positions (y-pitch). m denotes the number of times of repeated measurement of almost the same portion by the B-scan. Here, an initial position (x1, y1) can be set to any position by the input device 81 of FIG. 2.

In the present embodiment, the OCT apparatus performs a scanning method for repeating the B-scan for m times at almost the same portion to move to n-pieces of y-positions. Note that, the method of the repeated scanning may be a scanning method for repeating the A-scan at almost the same portion and then moving to a next position for performing the B-scan. Here, "Substantially a same position" includes an actual same position and almost same position. Ideally scanning is performed plural times at an actual same position. But in reality, scanning may be performed plural times at almost same position because of involuntary eye movement. If a tracking technique is used for tracking the eye movement, scanning may be performed plural times at almost same position because of imperfectness of the tracking technique.

When the number of times of repeated measurement m is large, the number of times of measurement at the same portion increases, so that accuracy of detecting the blood flow is enhanced. However, when the number of times of repeated measurement is too large, a scanning time becomes long and unintended effects of generating motion artifacts in an image because of movement of the eye (involuntary movement) during scanning and increasing the burden on a patient are caused. The present embodiment is carried out by setting m to 4 in consideration of a balance between the above-noted advantage and the disadvantages. Note that, m may be changed freely according to a velocity of the A-scan of the OCT apparatus and a moving amount of the eye of an object 100. That is, the number of times of repeated scanning is not limited to the aforementioned value.

An image size in the X-direction and the Y-direction is determined by p×n. When the image size in the X-direction and the Y-direction is large, scanning in a wide range is allowed if being performed at the same measurement pitch, but the scanning time becomes long and the aforementioned negative effects regarding motion artifact and the burden on a patient are caused. The present embodiment is carried out by setting n and p to 300 in consideration of both of the advantage and the disadvantage. Note that, n and p may be changed freely as appropriate. That is, the image sizes are not limited to the aforementioned value.

In the present embodiment, the x-pitch Δx and the y-pitch Δy are determined to be one half of a beam spot diameter of the irradiation light incident on the eye fundus, and is set as 10 μm, for example. In this case, scanning ranges of ΔXal1 and ΔYal1 may be represented by a multiplication of the pitch times the number of samples, according to the following formulas, and are respectively 3 mm, for example.

$$\Delta Xal1 = p \times \Delta x \quad \text{formula (1)}$$

$$\Delta Yal1 = n \times \Delta y \quad \text{formula (2)}$$

When Δx and Δy are set to be one half of the beam spot diameter on the eye fundus, a generated image can be formed with high definition. Even when Δx and Δy are set to be shorter than one half of the beam spot diameter on the eye fundus, an effect of further enhancing the definition of the generated image is small.

To the contrary, when the x-pitch and the y-pitch are set to be longer than one half of the beam spot diameter on the eye fundus, the definition is deteriorated, but it is possible to obtain an image in a wider range when a plane image size is the same. In response to a clinical request, Δx and Δy may be changed freely.

[Procedure for Obtaining Interfering Signal]

Next, one example of procedure for obtaining an interfering signal in the present embodiment will be described with reference to FIG. 5.

First, the CPU 80 sets an index i of a position yi of FIGS. 4 to 1 at step S109. Then, at step S110, the data obtaining unit 41 controls a driving mechanism (not illustrated) so that a scanning position of the X-axis scanner 53 and the Y-axis scanner 54 moves to (x1, yi) of FIG. 4.

The data obtaining unit 41 initializes an index j of the number of times of repeated measurement of the B-scan to 1 at step S119.

Then, at step S120, the data obtaining unit 41 controls the X-axis scanner 53 and the Y-axis scanner 54 to perform the B-scan for the j-th repeated measurement. A range of the B-scan is (x1, yi) to (xp, yi).

When a velocity of the A-scan is Fa[Hz], a net time of the B-scan (ΔtB) may be represented by the following formula with a use of the number of samples p in the x-scanning direction.

$$\Delta tB = \frac{p}{Fa} \qquad \text{formula (3)}$$

In the present embodiment, since Fa is 100 kHz and p is 300, ΔtB is 3 ms based on the formula (3).

A time interval of the repeated measurement (Δt) is obtained by adding a preparation time (Δtp) of the X-axis scanner 53 to the net time of the B-scan (ΔtB). Δt is represented by the following formula (4).

$$\Delta t = \Delta tp + \Delta tB \qquad \text{formula (4)}$$

Note that, the preparation time Δtp is, for example, a time for adjusting the scanning position of the X-axis scanner 53 and the Y-axis scanner 54. In the present embodiment, since Δtp is 1 ms, Δt is 4 ms based on the formula (4).

Further, the entire measurement time (tm) is represented by a following formula (5) with a use of the number of times of repeated measurement m, the number of samples n in the y-scanning direction, and the formula (4).

$$tm = \Delta t \times m \times n = (\Delta tp + \Delta tB) \times m \times n \qquad \text{formula (5)}$$

In the present embodiment, since m is 4 and n is 300, the entire measurement time tm is 4.8 s based on the formula (5).

In this case, as the time of the B-scan ΔtB and the time interval of the repeated measurement Δt are short, less influence of the movement of the object is received and bulk motion noise is reduced. To the contrary, as the time of the B-scan ΔtB and the time interval of the repeated measurement Δt are long, position reproducibility is lowered and the bulk motion noise increases because of the movement of the object. Further, a time required for the measurement becomes long and the burden on a patient becomes great. Here, the bulk motion means movement of the eye to be inspected and the bulk motion noise means noise generated by movement of the eye to be inspected.

Further, when the time interval of the repeated measurement Δt is too short, a time required for detecting the blood flow becomes short and sensitivity for detection of the blood flow is lowered.

It is desired that tm, Δt, n, p, ΔtB, and Δtp are selected in view of the above.

Note that, the X-axis scanner 53 and the Y-axis scanner 54 may perform the B-scan while following the object in order to enhance the position reproducibility of the repeated measurement.

At step S130, the difference detector 31 detects interfering light for each A-scan and the A/D converter 32 converts the interfering light to a digital signal (interfering signal). The data obtaining unit 41 obtains the interfering signal from the A/D converter 32 and stores the interfering signal in the storage device 84. The data obtaining unit 41 obtains p pieces of A-scan signals by one-time B-scan. The p pieces of A-scan signals form one B-scan signal.

At step S139, the data obtaining unit 41 increments the index j of the number of times of repeated measurement of the B-scan.

Then, the data obtaining unit 41 judges whether the index j is larger than the predetermined number of times of repeated measurement m at step S140. That is, the data obtaining unit 41 judges whether the B-scan is repeated for m times at the position yi. When not repeated, the procedure returns to step S120 at which the measurement of the B-scan at the same position is repeated. When repeated for the predetermined number of times, the procedure proceeds to step S149.

At step S149, the data obtaining unit 41 increments the index i of the position yi.

Then, at step S150, the data obtaining unit 41 judges whether the index i of the position yi is larger than the predetermined number of the measurement positions n, that is, whether the B-scan is performed at all the n pieces of y-positions. When the B-scan is not performed at all the n pieces of y-positions, the procedure returns to step S110 at which measurement is performed repeatedly at the next measurement position. When the B-scan is performed at all the n pieces of y-positions, the procedure proceeds to step S160.

The data obtaining unit 41 obtains background data at step S160. The data obtaining unit 41 controls a driving unit (not illustrated) to perform the A-scan for 100 times in a state where the shutter 56 is closed (state of being inserted into an optical path), and the data obtaining unit 41 averages 100 A-scan signals to store the resultant in the storage device 84. Note that, the number of times of background measurement is not limited to 100 times.

By performing the steps above, the data obtaining unit 41 is able to obtain a plurality of interfering signals obtained by performing repeated measurement of almost the same portion for at least two or more times, and the background data.

[Procedure for Signal Processing]

Next, one example of the procedure for signal processing will be described with reference to FIG. 6.

Figure 6:
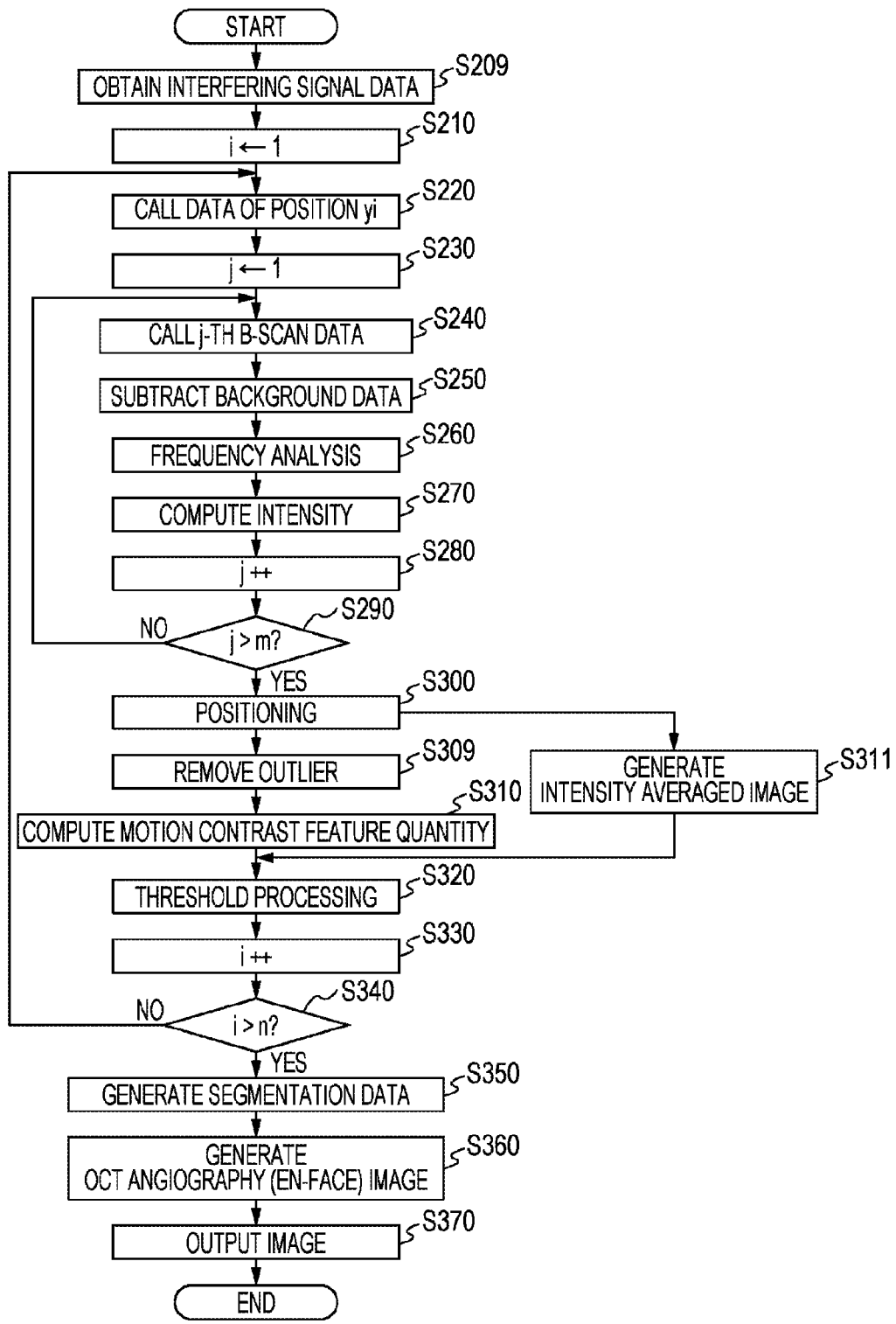
FIG. 6 is a flowchart illustrating a procedure of signal processing in the present embodiment.

FIG. 6 is a flowchart illustrating how the data obtaining unit 41 obtains an interfering signal, performs signal processing therefor, and then outputs an en-face image of the OCT angiography.

In the present embodiment, the motion contrast feature quantity needs to be computed to generate an en-face image of the OCT angiography.

At step S209 of FIG. 6, the data obtaining unit 41 obtains a plurality of interfering signals as a result of performing repeated measurement of almost the same portion for at least two or more times by the OCT apparatus. Note that, the data obtaining unit 41 may obtain interfering signals in accordance with the procedure for obtaining interfering signals described above or the data obtaining unit 41 may read interfering signals saved in the auxiliary storage device 87 in advance to obtain the interfering signals.

Then, the data obtaining unit 41 sets the index i of the position yi to 1 at step S210.

At step S220, the data obtaining unit 41 calls all the interfering signals of the B-scan (for m times), which are obtained by performing repeated measurement at the position yi.

At step S230, the data obtaining unit 41 then initializes the index j of the number of times of repeated measurement of the B-scan to 1.

At step S240, the data obtaining unit 41 calls a j-th interfering signal from the interfering signals of the B-scan for m times.

Figure 5:
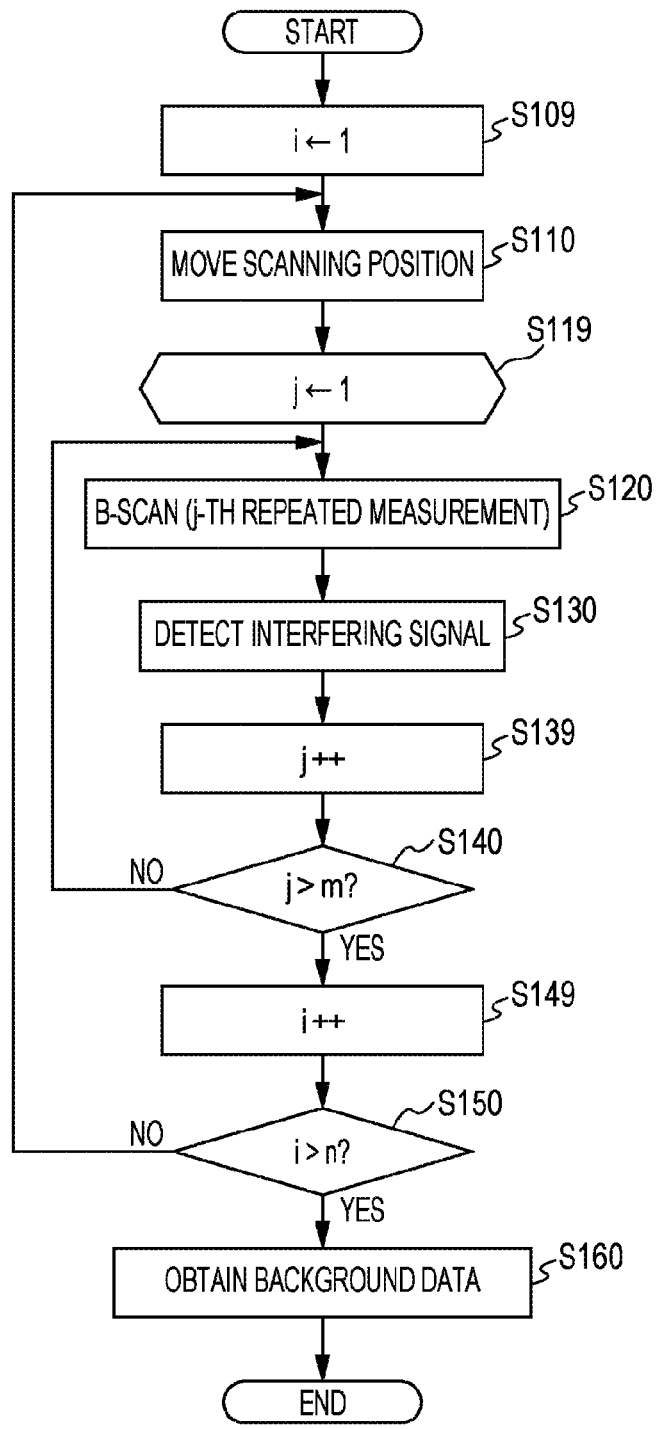
FIG. 5 is a flowchart illustrating one example of a procedure of measuring interfering signal data in the present embodiment.

Then, at step S250, the data obtaining unit 41 subtracts the background data obtained at step S160 of FIG. 5 from the interfering signal obtained at step S240.

At step S260, the analysis unit 43 performs frequency analysis for the interfering signal from which the background data is subtracted. In the present embodiment, an OCT complex signal composed of phase and amplitude is generated by applying Fast Fourier Transform (FFT) to the interfering signal as the frequency analysis. Note that, a maximum entropy method may be used for the frequency analysis.

At step S270, the analysis unit 43 computes the square of an absolute value of the OCT complex signal that has been subjected to the frequency analysis at step S260. A value of the square is an intensity of the tomographic image after the B-scan. That is, the analysis unit 43 obtains the tomographic image indicating the intensity at step S270.

At step S280, the data obtaining unit 41 increments the index j of the number of times of repeated measurement of the B-scan. Then, the data obtaining unit 41 judges whether the index j is larger than the predetermined number of times of repeated measurement m at step S290. When the index j is equal to or less than the predetermined number of times of repeated measurement m, the procedure returns to step S240 at which computation of the intensity of the B-scan by which the repeated measurement is performed at the same y-position is repeated. When the index j is larger than the predetermined number of times of repeated measurement m, the procedure proceeds to next step S300.

At step S300, the positioning unit 43 performs positioning of tomographic images for m frames of the B-scan, which are obtained by performing the repeated measurement at a certain position yi. Specifically, the positioning unit 43 selects any one tomographic image as a template from among the tomographic images for m frames. The positioning unit 43 may compute correlation between all combinations of the tomographic images for m frames, obtain a sum of correlation coefficients for each of the frames, and select a frame in which the sum is the largest.

Next, the positioning unit 43 compares the tomographic image selected as the template to the tomographic image of other frame and obtains a positional deviation amount ($\delta X$, $\delta Y$, $\delta \theta$). Specifically, the positioning unit 43 computes normalized cross-correlation (NCC) which is an index indicating similarity to the tomographic image of other frame while changing a position and an angle of the image as the template. The positioning unit 43 then obtains, as the positional deviation amount, a difference of positions between the images when a value of the NCC is the largest.

Note that, the index indicating the similarity may be variously changed as long as indicating the similarity of features between the image in other frame and the image as the template. For example, a Sum of Absolute Difference (SAD), or a Sum of Squared Difference (SSD) may be used as the index indicating the similarity. A Zero-means Normalized Cross-Correlation (ZNCC), or a Phase Only Correlation (POC) may be used as the index indicating the similarity. Further, a Rotation Invariant Phase Only Correlation (RIPOC) or the like may be used as the index indicating the similarity.

Next, the positioning unit 43 applies position correction to the tomographic image of the m−1 frame other than the template according to the positional deviation amount ($\delta X$, $\delta Y$, $\delta \theta$), and performs positioning of the tomographic images for the m frames.

At step S309, the removing unit 45 removes an outlier of the OCT complex signal, obtained from the result of the frequency analysis at step S260, with respect to pixel positions of the plurality of tomographic images obtained by repeatedly measuring almost the same portion for at least two or more times. In the present embodiment, the removing unit 45 removes the outlier from an output result of the computation of the intensity at step S270.

Figure 7:
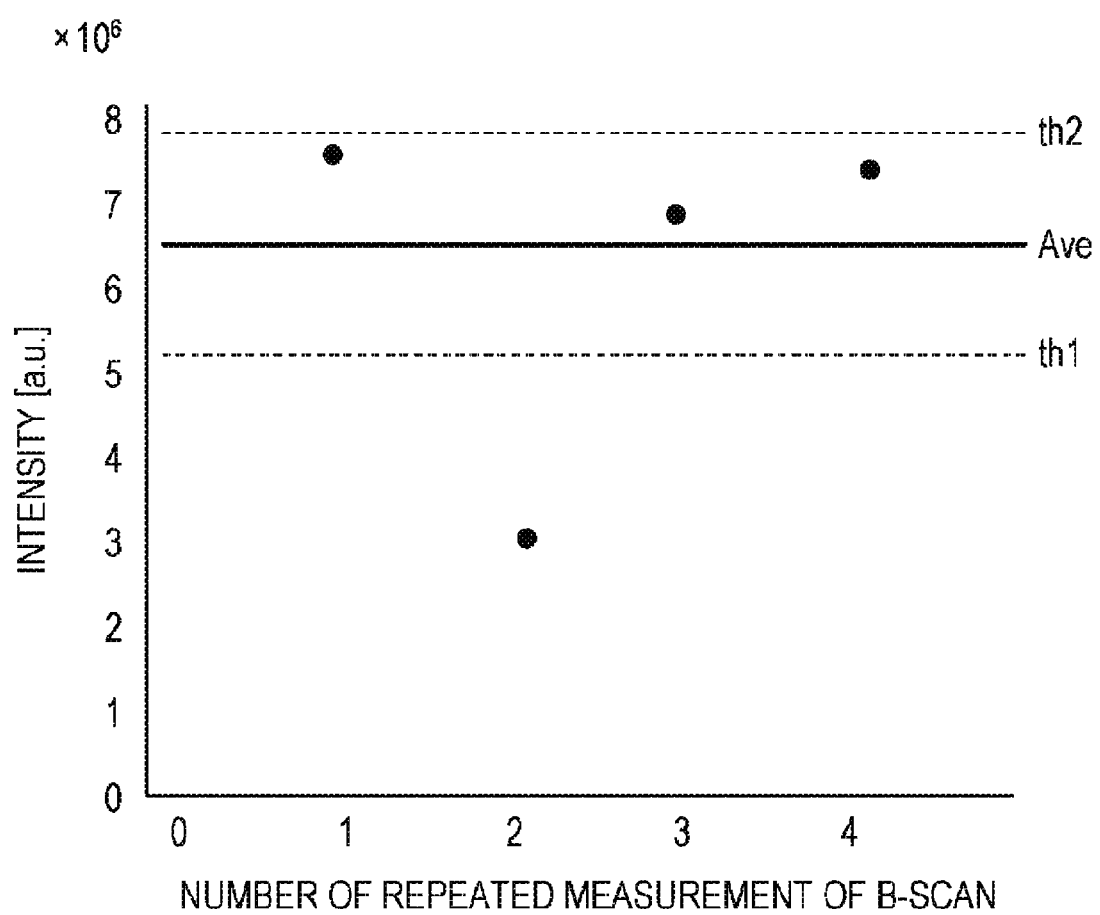
FIG. 7 is a diagram for explaining one example of a method for removing an outlier.

One example of removing the outlier will be described specifically with reference to FIG. 7. FIG. 7 illustrates one example of values of the intensity obtained by the repeated measurement for one pixel of a tomographic image. Here, each pixel is positioned at step S300. An axis of ordinates denotes the intensity and an axis of abscissae denotes a number of repeated measurement of the B-scan. The number of times of repeated measurement is four in the present embodiment.

An average value (Ave) and a standard deviation ($\delta$) of a plurality of intensities obtained by measuring almost the same portion are computed and thresholds (th1, th2) in FIG. 7 are set as the following formulas.

$$th1 = \text{Ave} - k \times \delta \qquad \text{formula (6)}$$

$$th2 = \text{Ave} + k \times \delta \qquad \text{formula (7)}$$

In the formulas, k is any setting parameter and is set as 1.2 in the present embodiment. Note that, the value of k is not limited to 1.2.

By using the thresholds th1 and th2 and setting the average value (Ave) of the intensities as a reference, the removing unit 45 removes a measurement value equal to or less than the threshold th1 and equal to or more than the threshold th2 as the outlier. That is, the outlier indicates a value exceeding the thresholds which are set. FIG. 7 indicates that data with the number of repeated measurement of 2 is the outlier. That is, the removing unit 45 removes, as the outlier, the signal intensity deviated by a predetermined value or more from the average value (Ave) of the signal intensities indicated by a plurality of tomographic images.

In this manner, the outlier is removed for each pixel of data of the tomographic images. Since the outlier is removed for each pixel, data effective for generating an image of the blood vessel is not removed unnecessarily. Thus, it is possible to achieve both noise reduction and generation of an image of the blood vessel with high accuracy.

Note that, a phase may be used instead of the intensity as a method for detecting and removing the outlier. In this case, the removing unit 45 removes, as the outlier, the phase deviated by a predetermined value or more from an average value of phases indicated by a plurality of pieces of tomographic image data.

In addition, the thresholds for determining the outlier may be determined freely.

After step S309 ends, the procedure proceeds to step S310.

At step S310, the computation unit 46 computes motion contrast feature quantities based on a data set from which the outlier is removed at step S309.

In the present embodiment, dispersion values of respective pixels at the same position are computed from the tomographic images (intensity images) of the m frames, which are positioned at step S300, and the dispersion values are used as the motion contrast feature quantities.

Note that, the motion contrast feature quantities may be obtained variously, and any types of motion contrast feature quantities are able to be applied to the invention as long as being an index indicating a change of a measurement value of each pixel, obtained by performing repeated measurement at the same y-position.

On the other hand, at step S311, the averaging unit 44 averages the tomographic images (intensity images) positioned at step S300 and generates an intensity averaged image.

At step S320, the threshold processing unit 47 performs threshold processing for the motion contrast feature quantities output at step S310. An area in which only random noise is displayed with a noise floor is extracted from the intensity averaged image output by the averaging unit 44 at step S311, the standard deviation $\delta$ is computed, and the average intensity of the noise floor +2 $\delta$ is set as a value of the threshold. The threshold processing unit 47 determines a region in which the intensity of each pixel is equal to or less than the threshold in the intensity averaged image. Then, the threshold processing unit 47 sets the motion contrast feature quantity corresponding to the determined region to 0. That is, the threshold processing unit 47 sets the value of the motion contrast feature quantity corresponding to the region in which the signal intensity is equal to or less than the threshold in the intensity averaged image among the motion contrast feature quantities computed at step S310 to 0.

By the threshold processing at step S320, the motion contrast derived from the change of the intensity due to the random noise is removed. This makes it possible to remove the motion contrast noise caused in an area having no object in the motion contrast image.

Note that, as the value of the threshold becomes small, the sensitivity for detection of the motion contrast increases, but the remaining motion contrast noise also increases. As the value of the threshold becomes great, the motion contrast noise decreases, but the sensitivity for detection of the motion contrast is lowered. The threshold is set as the average intensity of the noise floor +2 δ in the present embodiment, but the threshold is not limited thereto.

The data obtaining unit 41 increments the index i of the position yi at step S330.

At step S340, the data obtaining unit 41 judges whether the index i of the position yi is larger than the predetermined number of times of measurement n. When the index i is smaller than the predetermined number of times of measurement n, the procedure returns to step S220 at which processing of data at a next y-position is repeated. When the index i is larger than the number of times of measurement n, the procedure proceeds to step S350.

At a time point when step S340 ends, the averaged image and a B-scan image (two-dimensional data in the Z-depth direction and the X-direction) of the motion contrast feature quantity are obtained at all the y-positions. That is, the averaged image and three-dimensional data (volume data) of the motion contrast feature quantity are obtained.

At step S350, the segmentation unit 48 performs segmentation of the retina for the intensity averaged image generated by the averaging unit 44 at step S311. The segmentation of the retina will be specifically described below.

The segmentation unit 48 extracts the intensity averaged image to be subjected to processing, which is taken from the intensity averaged images of a plurality of y-positions. The segmentation unit 48 then applies a median filter and a SoBel filter to the extracted intensity averaged image to generate images (which are also respectively referred to as a median image and a SoBel image below).

Next, the segmentation unit 48 creates profiles for each A-scan from the created median image and SoBel image. The created profiles serve as a profile of a luminance value in the median image and a profile of gradient in the SoBel image. The segmentation unit 48 detects a peak in the profile created from the SoBel image. The segmentation unit 48 extracts boundaries between regions of the layer of the retina (layer boundaries) by referring to the profile of the median image corresponding to portions before and after the detected peaks or between the detected peaks.

The segmentation will be described with reference to FIG. 8. FIG. 8 illustrates an intensity averaged image at a certain y-position, in which segmentation lines are overlaid on the intensity averaged image with broken lines. Six layers are detected by the segmentation in the present embodiment. The six layers are (1) a nerve fiber layer (NFL), (2) a layer in which a ganglion cell layer (GCL) and an inner plexiform layer (IPL) are combined, (3) a layer in which an inner nuclear layer (INL) and an outer plexiform layer (OPL) are combined, (4) a layer in which an outer nuclear layer (ONL) and an external limiting membrane (ELM) are combined, (5) a layer in which an ellipsoid zone (EZ), an interdigitation zone (IZ), and a retinal pigment epithelium (RPE) are combined, and (6) a choroid.

Note that, the segmentation described in the present embodiment is one example and the segmentation may be performed by using other method such as Dijkstra method. The number of layers to be detected may be selected freely.

Referring back to FIG. 6, at step S360, the image generation unit 49 generates an OCT angiography image based on a result of the segmentation of the retina and the motion contrast feature quantity having been subjected to the threshold processing. For example, the image generation unit 49 generates the OCT angiography image (en-face image) based on the segmentation data output at step S350.

FIG. 9 illustrates an OCT angiography (en-face image) in the present embodiment. A method for generating the en-face image will be specifically described below.

The image generation unit 49 cuts out an area corresponding to, for example, the layer in which a ganglion cell layer (GCL) and an inner plexiform layer (IPL) are combined from volume data of the motion contrast feature quantity. Then, the image generation unit 49 computes a representative value of the motion contrast feature quantity for each A-scan. The representative value of the A-scan may be any of an average value, a highest value, and a median value. By projecting the representative value of the A-scan in the two-dimensional direction (the X-direction and the Y-direction), an enface image corresponding to (2) the layer in which the ganglion cell layer (GCL) and the inner plexiform layer (IPL) are combined is generated. Note that, since the motion contrast feature quantity and the result of the segmentation are obtained from the same tomographic image, the motion contrast feature quantity and the result of the segmentation are associated with each other. Thus, with the association of the motion contrast feature quantity and the result of the segmentation, the generation unit 44 is able to cut out a motion contrast feature quantity of any layer from three-dimensional volume data of the motion contrast feature quantity.

In the present embodiment, when plotting the representative value of the A-scan in the two-dimensional direction (the X-direction and the Y-direction), a value used for plotting the representative value of the A-scan is log-transformed to thereby broaden a dynamic range for display. Note that, the log transformation may not be performed.

FIG. 9 illustrates the en-face image obtained by measuring a macula by the OCT apparatus. In the present embodiment, the image generation unit 49 cuts out the motion contrast feature quantity of the layer in which the ganglion cell layer (GCL) and the inner plexiform layer (IPL) are combined from the three-dimensional volume data of the motion contrast feature quantity based on the result of the segmentation. Then, the image generation unit 49 projects or integrates the cut-out motion contrast feature quantity in the depth direction of the eye fundus to generate a motion en-face image. That is, the generation unit 44 projects or integrates a motion contrast value in the depth direction of the object based on the layer boundaries detected by the detection unit to generate a two-dimensional motion contrast image. As illustrated in FIG. 9, a portion with a high motion contrast feature quantity (a white portion in the image) visualizes the blood vessel of the eye fundus.

Note that, it is possible to generate an en-face image of any layer by selecting segmentation data.

Referring back to FIG. 6, at step S370, the display control unit 70 causes the output device 85 serving as a display to display the en-face image generated at step S360. Note that, though the en-face image is generated and displayed in the embodiment, a three-dimensional OCT angiography image or a partial three-dimensional OCT angiography image may be generated and displayed.

Figure 10A:
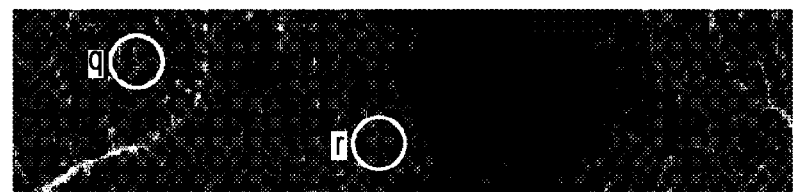
FIGS. 10A and 10B illustrate one example of an OCT angiography image to which the present embodiment is applied and an OCT angiography image to which the present embodiment is not applied.

Next, an effect of the present embodiment will be described with reference to FIGS. 10A and 10B. FIG. 10A illustrates an en-face image generated without performing the step of removing the outlier at step S309 by the removing unit 45 in the present embodiment. Horizontally linear bulk motion noises can be seen at each position of q and r.

Figure 10B:
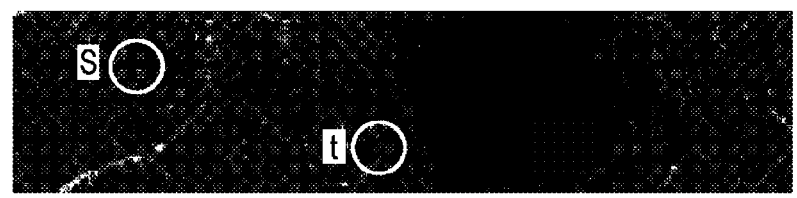

On the other hand, FIG. 10B illustrates an en-face image generated by performing the step of removing the outlier at step S309 as described above. The horizontally linear bulk motion noises are reduced at positions denoted by s and t which correspond to the same positions as the positions q and r.

In the present embodiment, by computing the motion contrast feature quantity with data from which the outlier of the OCT complex signal is removed, abnormal measurement data caused by measuring different portions because of generation of the bulk motion is removed. Thus, it is possible to reduce the bulk motion noise in the motion contrast image.

Accordingly, the present embodiment allows effective reduction of the bulk motion noise in the OCT angiography. That is, according to the present embodiment, it becomes possible to generate an image of a blood vessel accurately.

Second Embodiment

A second embodiment is different from the first embodiment in that the removing unit 45 obtains an approximation curve from a plurality of interfering signals obtained by repeatedly measuring almost the same portion for at least two or more times and removes an outlier with the approximation curve as a reference.

Figure 11:
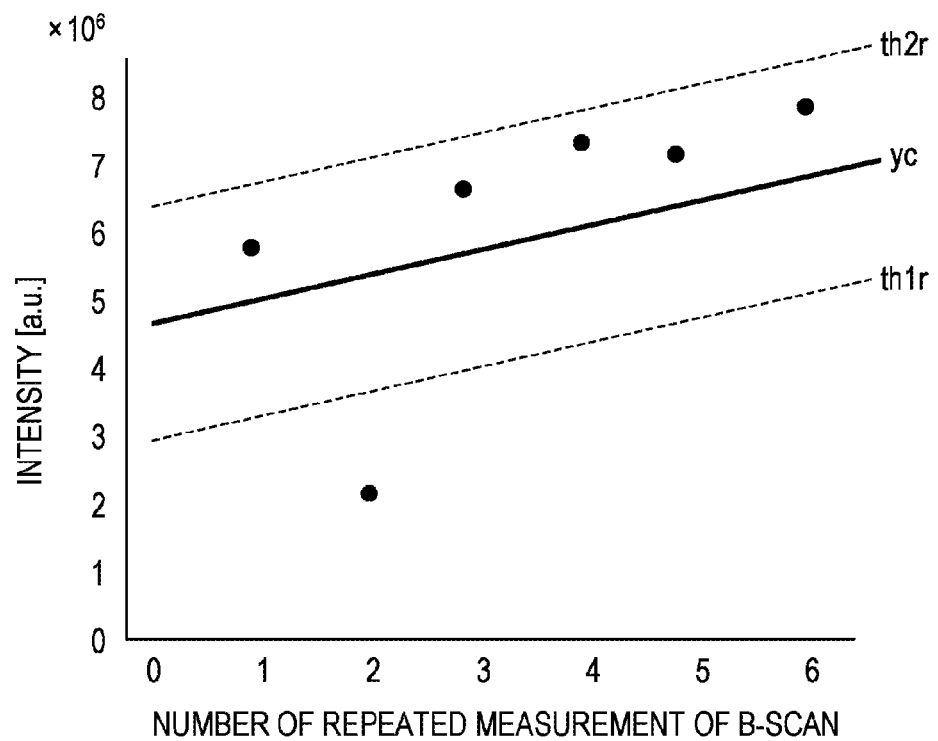
FIG. 11 is a diagram for explaining one example of a method for removing an outlier while considering trend.

The present embodiment will be described with reference to FIG. 11. In FIG. 11, an axis of ordinates denotes the intensity and an axis of abscissae denotes a number of repeated measurement of the B-scan. The number of times of repeated measurement m is six in the present embodiment. Note that, the number of times of repeated measurement of the B-scan is not limited to six.

A solid line yc in FIG. 11 is an approximation straight line computed by using six signal intensities by the removing unit 45. This approximation straight line yc can be represented by the following formula (8) with $\alpha$ as a constant and $\beta$ as a first-order coefficient.

$$yc = \alpha + \beta x \quad \text{formula (8)}$$

When a residual sum of squares of the approximation straight line yc is $\delta r^2$, the removing unit 45 sets thresholds of FIG. 11 (th1r, th2r) by the following formulas (9, 10).

$$th1r = yc - kr \times \delta r \quad \text{formula (9)}$$

$$th2r = yc + kr \times \delta r \quad \text{formula (10)}$$

In the formulas, kr is any setting parameter, and kr is set as 1.2 in the present embodiment. The removing unit 45 removes data whose measurement value is equal to or less than the threshold th1r and equal to or more than the threshold th2r as the outlier by using the formulas (8) and (9). Thereby, the outlier is removed with the approximation curve as the reference from a plurality of pieces of intensity data obtained by repeated measurement. FIG. 11 indicates that data with the number of repeated measurement of 2 is the outlier.

Note that, yc is the approximation straight line in the present embodiment, but may be an approximation curve of any order for enhancing accuracy for removing the outlier. That is, the removing unit 45 removes, as the outlier, the signal intensity deviated by a predetermined value or more from the approximation straight line or the approximation curve computed from the average value of the signal intensities indicated by a plurality of pieces of tomographic image data. Further, a phase may be used instead of the signal intensity. In this case, the removing unit 45 removes, as the outlier, the phase deviated by the predetermined value or more from the approximation straight line or the approximation curve computed from the average value of phases indicated by a plurality of pieces of tomographic image data.

The thresholds th1r and th2r may be set as a 95% confidence interval of the approximation straight line yc.

Accordingly, by removing the outlier from a plurality of pieces of interfering signal data obtained by repeated measurement with the approximation curve as the reference as in the present exemplary embodiment, even when data of the repeated measurement has trends, it is possible to effectively reduce the bulk motion noise in the OCT angiography. That is, according to the present embodiment, it becomes possible to generate an image of a blood vessel accurately.

Third Embodiment

A third embodiment of the invention has a characteristic that when outliers are detected at a certain percentage or higher in the same A-scan or a single frame, the outliers are removed in a unit of an A-scan line or a unit of a frame to compute a motion contrast. That is, the processing at step S309 in the first embodiment is changed.

The removing unit 45 in the present embodiment causes the storage device 84 to store a pixel position (pixel position x, y, z in volume data) at which the outlier is generated and a number of a frame of repeated measurement thereof. The removing unit 45 causes the storage device 84 to store the pixel position at which the outlier is determined and the outlier is caused and a number of a frame of repeated measurement thereof for all tomographic image data. For example, in the example illustrated in FIG. 7, the removing unit 45 causes the storage device 84 to store the frame number 2 and the pixel position of the outlier of the frame number 2.

Subsequently, the removing unit 45 computes a percentage of the outlier included in each A-can line or frame (percentage of including an outlier) at step S309.

Then, from the A-scan line or frame whose percentage of including an outlier is equal to or more than a fixed value (for example, 20%), the removing unit 45 removes tomographic image data of the corresponding region. That is, when outliers are detected at the fixed percentage or higher in the A-scan line or the frame, the removing unit 45 removes the outliers in a unit of the A-scan line or a unit of the frame.

Next, at step S310, the computation unit 46 computes the motion contrast feature quantity based on interfering signal data from which the outliers are removed at step S309. In the present exemplary embodiment, even when the position of repeated measurement is greatly deviated, the bulk motion noise can be removed accurately in a unit of the A-scan line or a unit of the frame in which the positional deviation is caused. Note that, the present embodiment may be combined with any of the first embodiment and the second embodiment.

Fourth Embodiment

A fourth embodiment has a characteristic that a portion at which an outlier is generated is displayed on an OCT angiography image.

Figure 12:
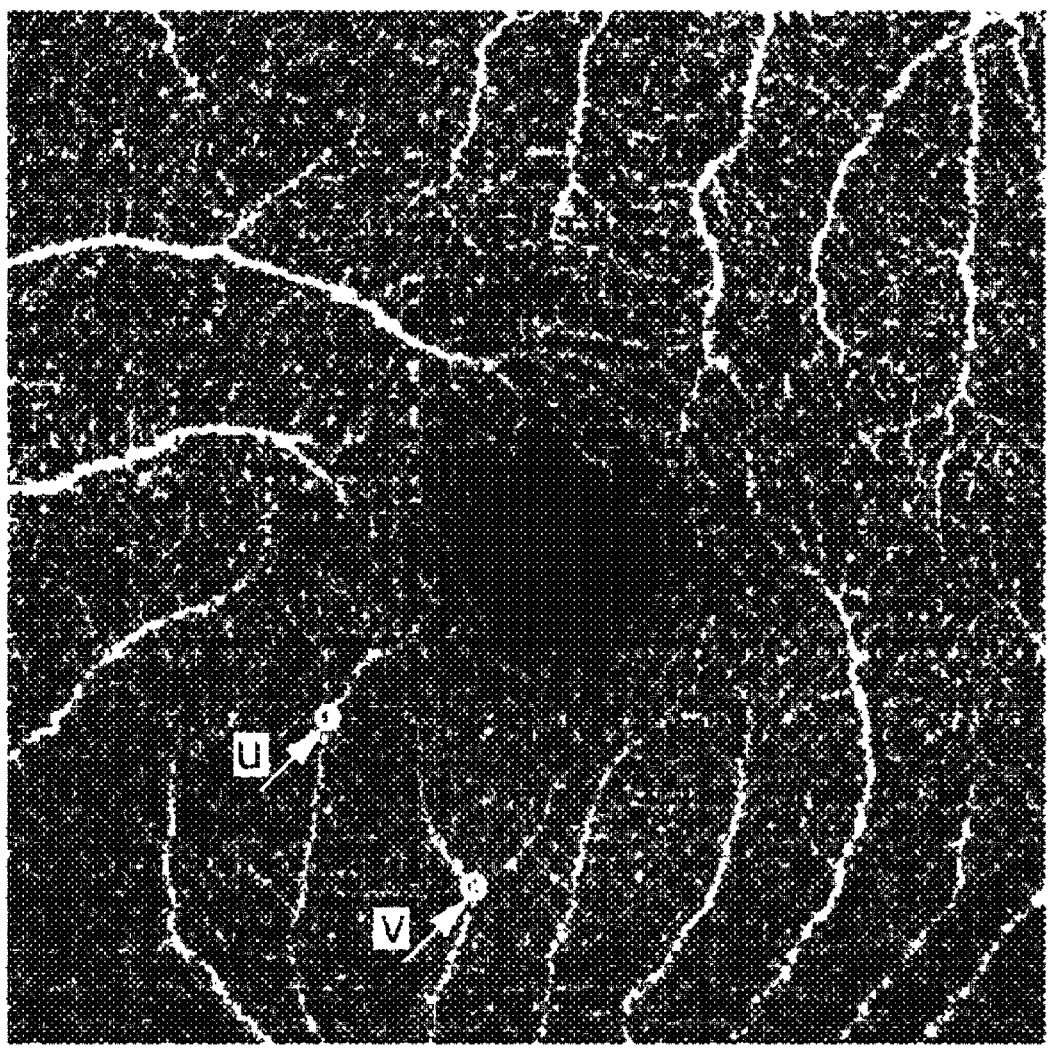
FIG. 12 illustrates one example of an OCT angiography image in the present embodiment.

The present embodiment will be described with reference to FIG. 12. In FIG. 12, the circular features pointed by arrows of markers u and v represent portions at which outliers are generated.

Specifically, similarly to the third embodiment, the removing unit 45 causes the storage device 84 to store pixel positions (pixel position x, y, z in volume data) at which the outliers are generated. The display control unit 70 causes the portions at which the outliers are removed to be displayed on the OCT angiography image based on the pixel positions at which the outliers are generated, which are stored in the storage device 84. That is, the display control unit 70 causes the portions at which the outliers are generated to be displayed on a motion contrast image.

Note that, the arrows are used as the markers in the example illustrated in FIG. 12, but any marker may be used. Whether or not to display a portion at which an outlier is generated can be decided freely. According to the present embodiment, an inspection operator is able to confirm a region in which an outlier is generated. Accordingly, it is possible to judge, for example, a reason why a clear image of a blood vessel is not generated is a disease or removal of an outlier.

Fifth Embodiment

A fifth embodiment has a characteristic that a pixel in which the given number or more of outliers are generated is regarded as an error, and the erroneous pixel is interpolated with a motion contrast value of an adjacent non-erroneous pixel.

Specifically, the removing unit 45 causes the storage device 84 to store the number of generated outliers in the same pixel and a position of the pixel. For example, when the signal intensity with the frame number of 3 is the outlier in the example illustrated in FIG. 7, the removing unit 45 causes the storage device 84 to store the number of generated outliers of two and the pixel position.

When the number of generated errors is the given number (for example, 2) or more, the pixel is regarded as an erroneous pixel, and the computation unit 46 obtains the number of generated outliers and the corresponding pixel position stored in the storage device 84 and linearly interpolates the erroneous pixel with a motion contrast value of the adjacent non-erroneous pixel. That is, the removing unit 45 causes the storage device 84 to store, as an erroneous region, the pixel in which the given number or more of outliers are generated, and the computation unit 46 interpolates the erroneous region.

Note that, other methods such as spline interpolation may be used for the interpolation. Note that, the interpolation may not be performed when there are the given number or more of erroneous pixels consecutively. That is, when the number of consecutive erroneous pixels is the given number or less, the computation unit 46 performs the interpolation. Note that, when there are the given number or more of erroneous pixels consecutively, a display indicating that there is an error may be performed on the OCT angiography image.

Moreover, the erroneous pixel may be processed as an erroneous region having a constant erroneous pixel density.

In the present embodiment, a pixel having the given number or more of outliers is regarded as an erroneous pixel and the pixel having low reliability is subjected to interpolation processing, thus making it possible to reduce the bulk motion noise in the OCT angiography.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-094343, filed on May 1, 2015 which is hereby incorporated by reference herein in its entirety.

What is claimed is:

1. A method of generating a motion contrast image using optical coherence tomography, comprising:
  a data obtaining step of obtaining a plurality of pieces of tomographic image data each indicating a tomogram at substantially the same portion of an object;
  a removing step of removing an outlier from the plurality of pieces of tomographic image data;
  a computation step of computing a motion contrast value based on the plurality of pieces of tomographic image data from which the outlier is removed; and
  a generation step of generating a motion contrast image of the object based on the motion contrast value.

2. The image generating method according to claim 1, wherein the plurality of pieces of tomographic image data is data obtained by performing frequency analysis for an output of a sensor which has received interfering light.

3. The image generating method according to claim 2, wherein performing the frequency analysis includes applying Fast Fourier Transform (FFT) to the interfering light.

4. The image generating method according to claim 3, further comprising:

a positioning step of positioning the plurality of pieces of tomographic image data, wherein the removing step is performed after the positioning step is performed.

5. The image generating method according to claim 3, wherein, at the removing step, when outliers are detected at a fixed percentage or higher in an A-scan line or a frame, the outliers are removed in a unit of the A-scan line or a unit of the frame.

6. The image generating method according to claim 2, further comprising:

a positioning step of positioning the plurality of pieces of tomographic image data, wherein the removing step is performed after the positioning step is performed.

7. The image generating method according to claim 6, wherein, at the removing step, when outliers are detected at a fixed percentage or higher in an A-scan line or a frame, the outliers are removed in a unit of the A-scan line or a unit of the frame.

8. The image generating method according to claim 2, wherein, at the removing step, when outliers are detected at a fixed percentage or higher in an A-scan line or a frame, the outliers are removed in a unit of the A-scan line or a unit of the frame.

9. The image generating method according to claim 1, further comprising:

a positioning step of positioning the plurality of pieces of tomographic image data, wherein the removing step is performed after the positioning step is performed.

10. The image generating method according to claim 9, wherein, at the removing step, when outliers are detected at a fixed percentage or higher in an A-scan line or a frame, the outliers are removed in a unit of the A-scan line or a unit of the frame.

11. The image generating method according to claim 1, wherein, at the removing step, a signal intensity deviated by a predetermined value or more from an average value of signal intensities indicated by the plurality of pieces of tomographic image data is removed as the outlier.

12. The image generating method according to claim 1, wherein, at the removing step, a phase deviated by a predetermined value or more from an average value of phases indicated by the plurality of pieces of tomographic image data is removed as the outlier.

13. The image generating method according to claim 1, wherein, at the removing step, a signal intensity deviated by a predetermined value or more from an approximation straight line or an approximation curve computed from an average value of signal intensities indicated by the plurality of pieces of tomographic image data is removed as the outlier.

14. The image generating method according to claim 1, wherein, at the removing step, a phase deviated by a predetermined value or more from an approximation straight line or an approximation curve computed from an average value of phases indicated by the plurality of pieces of tomographic image data is removed as the outlier.

15. The image generating method according to claim 1, wherein, at the computation step, variation of signal intensities or phases between the plurality of pieces of tomographic image data is computed as a motion contrast feature quantity.

16. The image generating method according to claim 1, wherein, at the removing step, when outliers are detected at a fixed percentage or higher in an A-scan line or a frame, the outliers are removed in a unit of the A-scan line or a unit of the frame.

17. The image generating method according to claim 1, further comprising:

a display control step of causing a display unit to display a motion contrast image generated at the generation step, wherein at the display control step, a portion at which the outlier is generated is displayed on the motion contrast image.

18. The image generating method according to claim 1, wherein at the removing step, a pixel of a region in which a predetermined number of outliers are generated is stored as an erroneous region, and at the computation step, the erroneous region is interpolated with a motion contrast value of an adjacent non-erroneous pixel.

19. An image generating apparatus, comprising:

a data obtaining unit configured to obtain a plurality of pieces of tomographic image data each indicating a tomogram at substantially the same position of an object;

a removing unit configured to remove an outlier from the plurality of pieces of tomographic image data;

a computation unit configured to compute a motion contrast value based on the plurality of pieces of tomographic image data from which the outlier is removed; and a generation unit configured to generate a motion contrast image of the object based on the motion contrast value.

20. A recording medium non-transitory storing therein a program for causing a computer to execute the steps of the image generating method according to claim 1.

* * * * *